(12) United States Patent
Kumar et al.

(10) Patent No.: US 11,701,283 B2
(45) Date of Patent: Jul. 18, 2023

(54) POSITIONING DEVICE FOR SUPPORTING AND STABILIZING A SPINAL POSITION OF A PATIENT

(71) Applicant: The Aga Khan University, Karachi (PK)

(72) Inventors: Dileep Kumar, Karachi (PK); Saleem Sayani, Wynnewood, PA (US); Muhammad Abdul Muqeet, Karachi (PK); Hafiz Imtiaz Ahmed, Karachi (PK); Faizan Khan, North Nazimabad (PK)

(73) Assignee: The Aga Khan University, Karachi (PK)

( * ) Notice: Subject to any disclaimer, the term of this patent is extended or adjusted under 35 U.S.C. 154(b) by 219 days.

(21) Appl. No.: 16/667,806

(22) Filed: Oct. 29, 2019

(65) Prior Publication Data

US 2021/0077333 A1    Mar. 18, 2021

(30) Foreign Application Priority Data

Sep. 16, 2019    (PK) .................................... 626/2019

(51) Int. Cl.
*A61G 15/00* (2006.01)
*A61G 15/12* (2006.01)
(Continued)

(52) U.S. Cl.
CPC .......... *A61G 15/12* (2013.01); *A61B 17/3401* (2013.01); *A61G 15/10* (2013.01); *A61G 15/125* (2013.01)

(58) Field of Classification Search
CPC .... A47C 7/36; A47C 7/38; A47C 7/62; A47C 7/622; A47C 7/68; A47C 7/72;
(Continued)

(56) References Cited

U.S. PATENT DOCUMENTS 5,295,728 A * 3/1994 Schaevitz .............. A47C 9/025
297/195.1
5,971,485 A * 10/1999 Clark ................... A61G 13/009
297/195.11

(Continued)

OTHER PUBLICATIONS

Fettes et al., "Failed spinal anaesthesia: Mechanisms, management, and prevention," BJA: British Journal of Anaesthesia, Jun. 2009, 102(6):739-748.
(Continued)

*Primary Examiner* — Adam Baker
(74) *Attorney, Agent, or Firm* — Fish & Richardson P.C.

(57) ABSTRACT

A positioning device includes a base extending in a horizontal plane, a support post extending along a vertical axis, a detachable headrest subassembly attached to an end of the support post opposite the base, an arm rest subassembly attached to the support post between the headrest subassembly and the base, a thoracic support subassembly attached to the support post between the armrest subassembly and the base, A thoracic support cushion is attached to the support post by a bar. The attachment is reconfigurable to vary an orientation and location of the cushion with respect to the vertical axis, a footrest subassembly attached to the support post between the thoracic support subassembly and the base, and a digital device holder attached to the positioned device by a flexible arm, the flexible arm configured to support a digital device in view of the patient during use of the positioning device.

20 Claims, 13 Drawing Sheets

(51) Int. Cl.
*A61B 17/34* (2006.01)
*A61G 15/10* (2006.01)

(58) Field of Classification Search
CPC ......... A47C 7/723; A47C 7/725; A47C 9/005; A47C 9/002; A61G 13/12; A61G 13/121; A61G 13/122; A61G 13/1225; A61G 13/1235; A61G 13/009; A61G 13/0054; A61G 15/12; A61G 15/125; A61G 15/10; A61G 15/14; A61G 2200/327; A61G 2200/50; A61G 2200/56; A61G 2200/325; A61G 13/1205; A61G 15/002; A61G 15/007; A61G 15/02; A61H 1/02; A61H 1/0214; A61H 1/0229; A61H 1/0292; A61H 1/0296; A61H 2201/0149
USPC .......................................... 128/845; 601/24
See application file for complete search history.

(56) References Cited

U.S. PATENT DOCUMENTS

| | | | | |
|---|---|---|---|---|
| 6,595,590 | B2* | 7/2003 | Bottoms | A47C 9/027 |
| | | | | 297/451.3 |
| 6,729,690 | B2* | 5/2004 | Roleder | A47C 9/005 |
| | | | | 297/16.1 |
| 6,758,447 | B2 | 7/2004 | Tinsley | |
| 7,080,885 | B2* | 7/2006 | Bain | A47C 1/03 |
| | | | | 297/354.1 |
| 8,365,739 | B1 | 2/2013 | Jones | |
| 2002/0020018 | A1 | 2/2002 | Heimbrock | |
| 2003/0090131 | A1* | 5/2003 | Roleder | A47C 9/005 |
| | | | | 297/195.11 |
| 2003/0090132 | A1* | 5/2003 | Dixon | A61G 7/065 |
| | | | | 297/195.11 |
| 2007/0052275 | A1* | 3/2007 | Ghilzai | A47C 1/11 |
| | | | | 297/423.12 |
| 2014/0252812 | A1* | 9/2014 | Ton | F16M 11/40 |
| | | | | 297/170 |
| 2015/0190265 | A1* | 7/2015 | Kreuzer | A61H 1/0218 |
| | | | | 602/33 |
| 2015/0335939 | A1* | 11/2015 | Pederson | A63B 71/0036 |
| | | | | 482/104 |

OTHER PUBLICATIONS

Parikh et al., "Approach to failed spinal anaesthesia for caesarean section," Indian Journal of Anaesthesia, Sep. 2018, 62(9):691-697.
Phsmedicalsolutions.com [online], "EPD Package 2—Epidural Positioning Device," available on or before Oct. 28, 2020, via Internet Archive: Wayback Machine URL <https://web.archive.org/web/20200801000000*/https://www.phsmedicalsolutions.com/products/_epidural-positioning-devices/epd-package-2>, retrieved on Jan. 5, 2022, URL<https://www.phsmedicalsolutions.com/products/_epidural-positioning-devices/epd-package-2>, 2 pages.

* cited by examiner

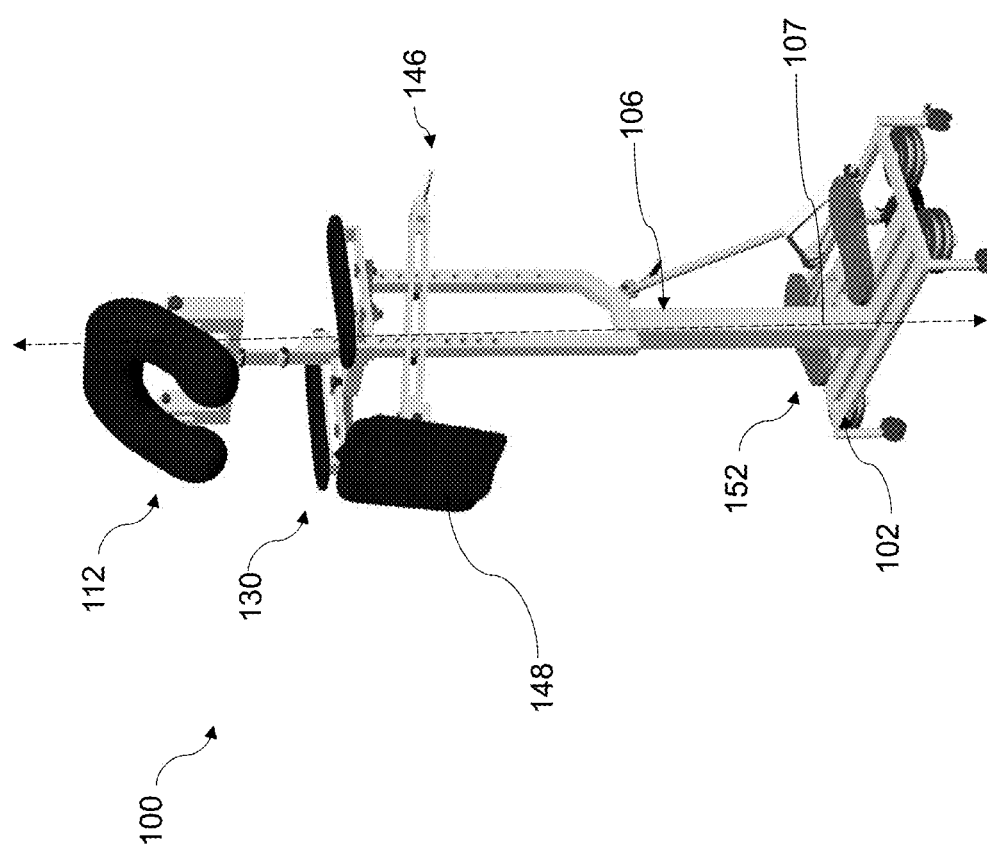

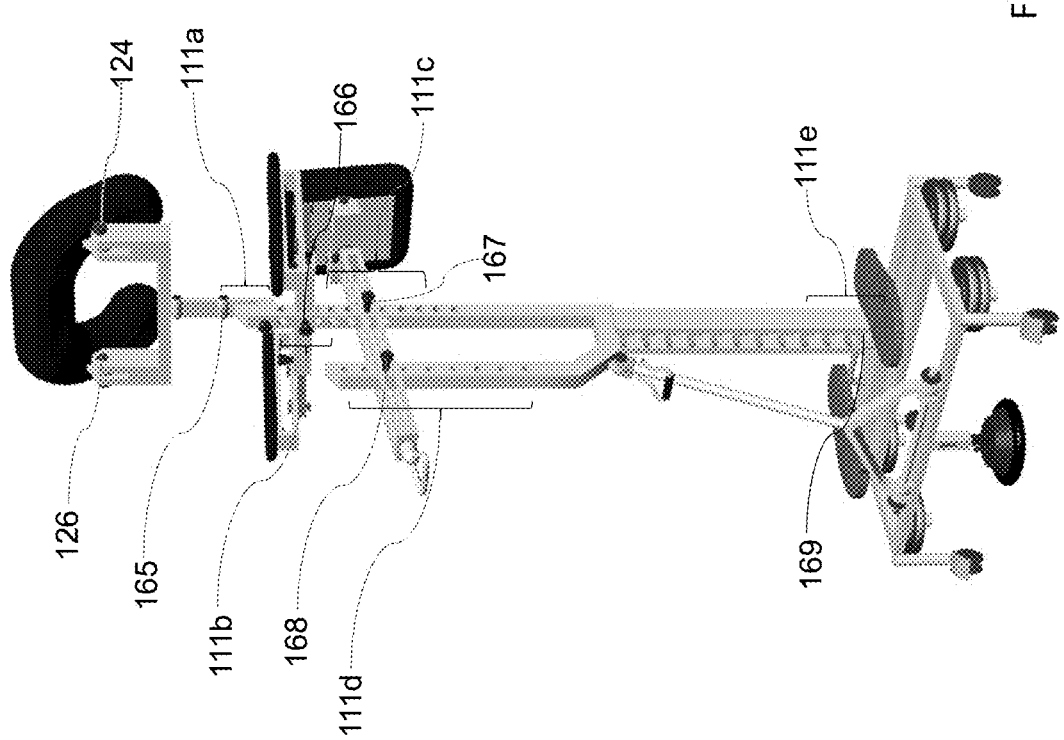

POSITIONING DEVICE FOR SUPPORTING AND STABILIZING A SPINAL POSITION OF A PATIENT

CROSS-REFERENCE TO RELATED APPLICATION

This disclosure claims priority to Pakistan Patent Application No. 626/2019, entitled "Positioning Device for Supporting and Stabilizing a Spinal Position of a Patient" and filed on Sep. 16, 2019, the entire contents of which is incorporated herein by reference.

TECHNICAL FIELD

This disclosure relates to a positioning device that can be used in spinal and epidural procedures.

BACKGROUND

Spinal and epidural procedures are routinely practiced by anesthesiologists in clinical settings, such as a labor and delivery suite, operating rooms for acute surgical pain, and for chronic neuropathic pain. The spinal and epidural procedure is called a central neurological interventional procedure or a central neuraxial blockade, and generally includes inserting a therapeutic needle to infiltrate the local anesthetic medicine in subarachnoid and epidural space to relieve the surgical and non-surgical pain. Typically, spinal anesthesia is performed by spinal needles to locate the subarachnoid space in lower lumber spine. An epidural is performed by epidural needles that locate the thin potential epidural space and dispense the local anesthetic medicines as a single shot technique. Alternatively, the epidural procedure places the continuous dispensing epidural catheter via epidural needle to achieve the continuous epidural anesthesia and analgesia. The spinal and epidural procedure can be performed in sitting and lateral position.

Such procedures are often performed on the lower lumbar region of spines in pregnant women to relieve labor and childbirth pain. The procedures are also performed on the cervical and thoracic regions of spines to relieve acute surgical pain and to treat chronic pain conditions in both males and females.

SUMMARY

The success of spinal and epidural procedures is generally dependent on the patient's anatomical spinal curvature, patient's immobility, understanding of procedural steps and patient-operator close loop communication. The disclosed positioning device can be used for successful procedures by providing a desired sitting position arrangement along with facilitating the patient's comprehensive involvement, among other features.

In certain aspects, a positioning device facilitates stable positioning of a patient in a sitting position for performance of epidural or spinal procedures. The positioning device includes a base extending in a horizontal plane, a support post extending along (e.g., parallel to) a vertical axis, a detachable headrest subassembly attached to an end of the support post opposite the base, an arm rest subassembly attached to the support post between the headrest subassembly and the base, a thoracic support subassembly attached to the support post between the armrest subassembly and the base, the thoracic support subassembly includes a thoracic support cushion attached to the support post by a bar, the attachment of the bar to the support post being reconfigurable to vary an orientation and location of the cushion with respect to the vertical axis, a footrest subassembly attached to the support post between the thoracic support subassembly and the base, and a digital device holder attached to the positioned device by a flexible arm, the flexible arm configured to support a digital device in view of the patient during use of the positioning device.

In some embodiments, the headrest subassembly includes a C-shaped cushion for supporting the patient's head during use.

In some embodiments, the headrest subassembly includes a chin support and a forehead support arranged to support the patients head relative to the digital device holder so that the patient can view the digital device during use of the positioning device.

In some embodiments, the support post includes a forked portion includes a pair of tines extending parallel to each other. In some embodiments, the thoracic support subassembly attaches to the support post at the tines. In some embodiments, the locations of attachment of the bar to each tine are adjustable.

In some embodiments, the armrest subassembly includes a pair of armrest cushions separated by a bar attached to the support post. In some embodiments, a width of the bar separating the armrest cushions is adjustable. In some embodiments, a position of the bar separating the armrest cushions along the vertical axis is adjustable.

In some embodiments, the base includes rollers for transporting the positioning device.

In some embodiments, the positioning device further includes a handle subassembly attached to the base separate from the support post.

In some embodiments, the positioning device further includes a suction cup extending from the base, configured to engage with a receiver. In some embodiments, the receiver is a floor. In some embodiments, the floor is a flat, horizontal surface.

In some embodiments, the positioning device further includes weighted plates arranged on the base of the position device.

To perform a spinal or epidural procedure using the positing device, the patient sits at the midpoint of the operating table or at the operator's edge/side of the operating table. Legs of the patient extend over a side edge, knees of the patient are bent, and feet of the patient are supported. Among other advantages, the positioning device provides rigid support and stabilizes the patient to orient the spine into the correct position. The positioning device may decrease the mobility of the patient and reduce movement of the patient during the procedure. This reduced movement can further reduce complications such as, multiple needle insertion attempts, accidental puncture of spinal cord coverings, hematoma, inadequate anesthesia and analgesia, nerve damage risk, and procedure failure.

The positioning device may also help the overcome a language barrier between the patient and the medical staff by providing a digital device, in the field of view of the patient, that demonstrates proper orientation and provides translational tools. The headrests provide a wide field of view that may increase patient balance, display a digital device for instructions or distraction, and reduce anxiety in claustrophobic patients. Further, the positioning device may reduce the anxiety of a patient by displaying videos, reading material, or other distractions on the digital device.

The positioning device may further increase patient comfort and reduce patient movement by providing adjustable subassemblies that reconfigure based on arm length, arm mobility, neck length, neck mobility, leg length, leg mobility, spinal region location (e.g., thoracic and lumbar), and spine mobility.

The positioning device can also improve the orientation of the spine in patients with limited spine mobility, for example pregnant and obese patients, by displaying the proper orientation on a digital device and adjusting subassemblies of the positioning device. The positioning device has detachable headrest subassemblies so that the positioning device can be used with a variety of headrest shapes. Different headrest subassemblies can each be used in cervical, thoracic, and lumbar spinal procedures to position the spine. Some headrests may increase comfort while other headrests may increase the patient's visibility. The positioning device also includes wheels and a handle so that the positioning device can be easily transported and steered without straining the subassemblies of the positioning device.

The details of one or more embodiments are set forth in the accompanying drawings and the description below. Other features, objects, and advantages of the implementations described herein will be apparent from the description, the drawings, and the claims.

DESCRIPTION OF DRAWINGS

FIGS. 1A-1D are perspective views of an example positioning device.

Like reference symbols in the various drawings indicate like elements.

DETAILED DESCRIPTION

Figure 1B:
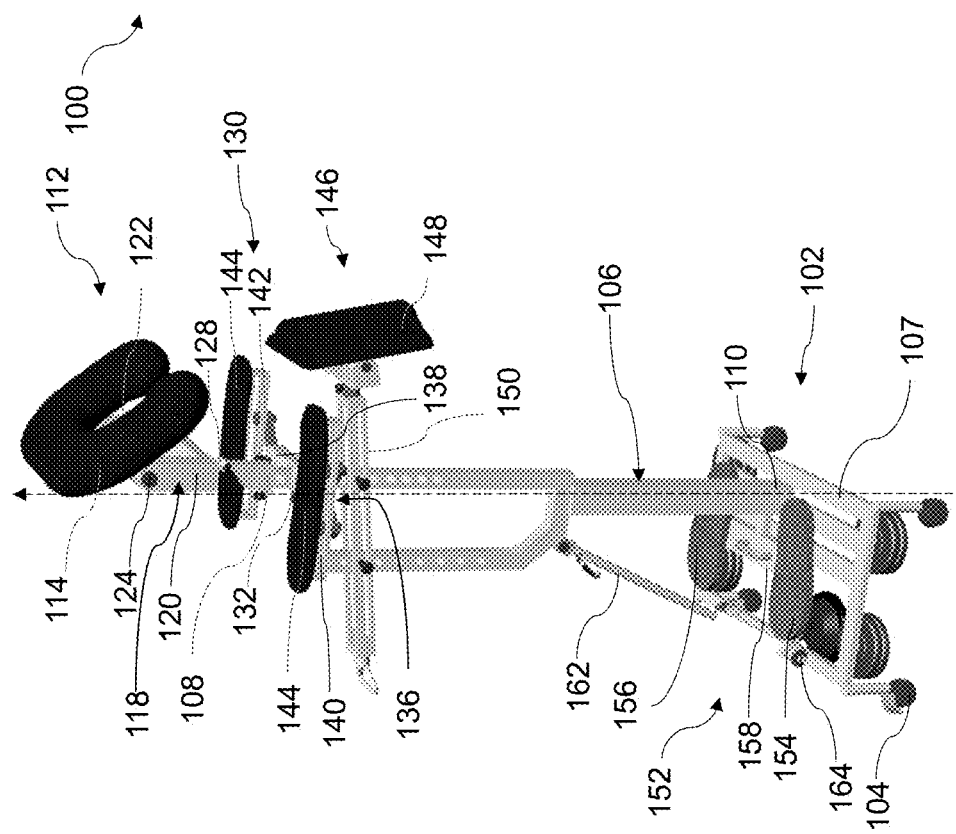

A positioning device facilitates appropriate and comfortable positioning for the spinal and epidural placement in pregnant and non-pregnant patients. The positioning device includes multiple adjustable subassemblies and components that orient a spine of a patient into a specific position for treatment, for example during an epidural procedure. The positioning device stabilizes the cervical, thoracic, and/or lumbar sections of the spine by orienting the neck, pelvis, and chest into a specific alignment. The procedure can be performed in the lower lumbar region of spines in pregnant women to relieve labor and childbirth pain. The procedure can also be performed in the cervical, thoracic and lumbar regions of the spine to relieve acute surgical pain and to treat chronic pain conditions in males and females.

FIGS. 1A-1D are perspective views of a positioning device 100 to facilitate stable positioning of a patient in a sitting position for performance of epidural or spinal procedures. The positioning device 100 is sufficiently tall to conform to a patient sitting on a hospital bed. For example, in the tallest position, device 100 can be 4.5-5.5 feet tall. The height can be adjusted, e.g., 12 to 24 inches, to accommodate different patients and different hospital beds. The positioning device 100 includes a base 102 that extends in a horizontal plane, i.e., the plane of the floor when the device is upright, providing a stable platform for the positioning device. The base 102 has rollers 104 to move the positioning device. The wheels have engagable locks 105 to prevent movement of the positioning device 100 during a procedure.

A support post 106 extends from the base 102 along (e.g., parallel to) a vertical axis 107. The support post 106 has a first end 108 opposite the base 102 and a second end 110 that attaches to the base 102. The support post 106 is "Y shaped" or forked, with a base section 106a, a first tine 106b extending from the base section 106a, and a second tine 106c extending from the base section 106a. The first tine 106b and the second tine 106c are parallel and extend towards the first end 108. The first tine 106b is longer in length that the second tine 106c.

The support post 106 has multiple (e.g., five) connection areas 111, shown on FIG. 1C, to which subassemblies, shown in FIG. 1A, of the positioning device 100 connect. In the present example, first, second, and third connection areas 111a, 111b, and 111c are located on the first tine 106b of the support post 106. A fourth connection area 111d is located on the second tine 106c of the support post 106 and a fifth connection area 106e is located on the base section 106a of the support post 106. The connection areas 111 are a vertical series of holes or notches that extend through the support post.

A detachable headrest subassembly 112 releasably attaches to the first end 108 of the support post 106 at the first connection area 111a. The headrest subassembly 112 includes a C-shaped headrest 114 that supports the outer edges of a face of the patient and leaves the chin unsupported. The patient, when in the proper position, can at least partially see through a central aperture 116 of the headrest 114. The headrest 114 is hingably attached to a frame 118. The frame 118 is U-shaped and connects at a first end 120 and at a second end 122 to the headrest 114 by a first hinge 124 and a second hinge 126, respectively. The first and second hinges 124, 126 are aligned so that the headrest 114 rotates about the hinges 124, 126 from 0° to 90° relative to the vertical axis 107. A rod 128 projects from the frame 118 at a midpoint equidistance from the first end 120 and the second end 122. The rod 128 protrudes from the frame, opposite the headrest 114, and includes a hinge 178. The rod 128 protrudes in the direction opposite the headrest 114 and may be welded, integrally formed, or otherwise permanently attached to the frame 118. The headrest subassembly 112 attaches to the support post 106 using by inserting the rod 128 into an opening defined in the first end 108 of the support post 106. A detailed description of attaching and detaching the headrest subassembly 112 is described below in the description of FIG. 8.

In use, the patient bows his/her head to flex and orient the cervical spine. The headrest 114 facilitates the flexion of the thoracic, and ultimately the lumbar, spines by flexing the cervical spine. Once the cervical spine is in the correct orientation, the hinges 124, 126, 178 are locked to prevent rotation of the headrest 114 during a procedure.

An arm support subassembly 130 attaches to the support post 106 at the second connection area 111b and extends along a horizontal plane, substantially parallel to the horizontal plane of the base 102. The arm support subassembly 130 includes a central bar 132 that defines a central opening 134 (shown in FIG. 7A) for receiving the support post 106. The central bar 132 has a first end 136 and a second end 138. A first plate 140 bolts to the first end 136 of the central bar 132. A second plate 142 bolts to the second end 138 of the central bar 132. The plates 140, 142 receive cushions 144 to increase patient comfort. The attachment of the central bar 132 to the support post 106 is reconfigurable to vary a location of the plates 140, 142 and cushions 144 with respect to the vertical axis 107. In some cases, the plates are arranged at an angle relative to the central bar 132.

In use, the patient places his/her arms on the cushions 144 of the arm support subassembly 130. The operator, for example a nurse, clinician, or doctor, readjusts the position of the arm support subassembly 130 to a comfortable height.

A support subassembly attaches to the support post 106 between the armrest subassembly 130 and the base 102 at the third connection area 111c and the fourth connection area 111d. The support subassembly orients and supports a portion of the spine. In the positioning device 100, the support subassembly is a thoracic/lumbar support subassembly 146. The thoracic/lumbar support subassembly 146 includes a thoracic support cushion 148 attached to the support post 106 by a support bar 150. The attachment of the support bar 150 to the support post 106 is reconfigurable to vary an orientation and location of the thoracic support cushion 148 with respect to the vertical axis 107. The thoracic support cushion 148 supports, orients, and stabilizes the thoracic spine of the patient. The thoracic support cushion 148 is releasably mounted on a hinge 200 of the support bar 150 and can be interchanged with other cushions. The hinge 200 is lockable. The cushion 148 is used during cervical, thoracic, and lumber spinal procedures with pregnant patients or obese patients. In use, the cushion 148 fits between the breasts and to avoid the direct pressure on breasts.

Figure 1D:
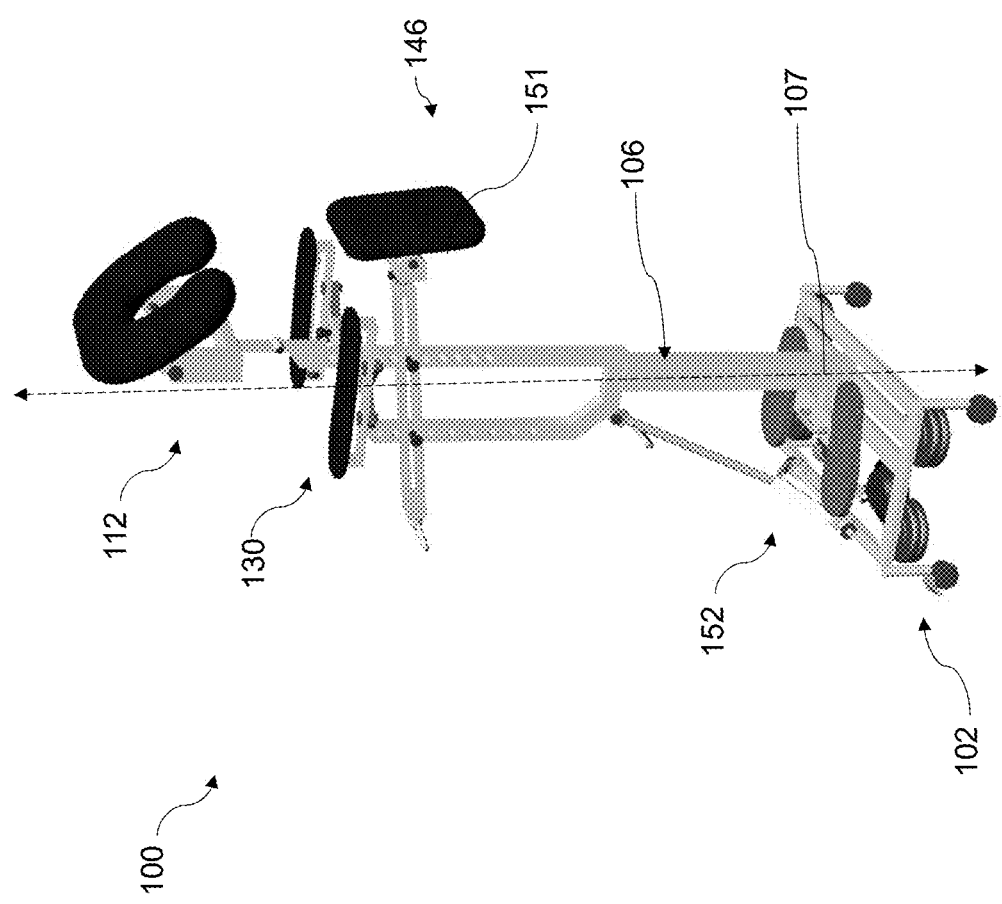

The thoracic/lumbar support subassembly 146 also includes a lumbar cushion 151 releasably mounted on the support bar 150 in place of the thoracic support cushion 148. This configuration is seen in FIG. 1D. The support bar 150 can be reconfigured as described previously with reference to the thoracic support cushion 148, for example to translate the lumbar cushion 151 vertically or angle the lumbar cushion 151 relative to the vertical axis 107. The lumbar cushion 151 is mounted onto the hinge 200 of the support bar 150 so that the cushion 151 can be angled relative to the vertical axis. This configuration is used during cervical, thoracic and lumber spinal procedures in males and in non-pregnant females. The lumbar cushion 151 is designed to abut a male chest and abdomen or non-pregnant female abdomen to support and orient the lumbar spine.

In use, the thoracic/lumbar support subassembly 146 is reconfigurable to translate the thoracic support cushion 148 towards or away from the patient, along the first tine 106b of the support post 106, or angle the thoracic support cushion 148 relative to the vertical axis 107.

A footrest subassembly 152 attaches to the support post 106 between the thoracic/lumbar support subassembly 146 and the base 102 at the fifth connection area 106e on the support post 106. The footrest subassembly 152 includes a left footrest 154 and a right footrest 156 that each support a foot of the patient during the procedure. The footrest subassembly 152 has a footrest bar 158 that connects the left footrest 154 and the right footrest 156. Some footrests had straps to restrain movement of the foot. A tongue 202 if the footrest bar 158 (shown in FIG. 5) is sized to be inserted into the base section 106a of the support post 106. The footrest subassembly 152 translates along the base section 106a of the support post 106 to reconfigure based on the leg length of the patient. A handle 162 hingably attaches to the base 102.

The positioning device properly aligns the spine, neck, legs, and arms of a patient during a spinal procedure. The patient first sits on the edge of an operating table and the positioning device is moved in front of the patient using the handle 162. The rollers 104 are locked. The patient places his/her head on the headrest 114 and places his/her feet on the left and right footrests 154, 156. An operator unlocks the footrest subassembly and adjusts the height of the footrest subassembly 152 to ensure that the legs are slightly bent. Unsupported and stretched legs put pressure on the hip joint and on sacral vertebras which prevents the flexion of spinal curvature. Slightly bent legs, supported by the footrests 154, 156, flex the hip joint and allow lumbar curvature.

The operator then locks the footrest subassembly 152 at the proper height. The operator also unlocks the headrest subassembly 112 and adjusts the height of the headrest subassembly 112. Once the correct height is found, the operator locks the headrest subassembly. The operator then sets the angle of the headrest 114 by unlocking the hinges 124, 126 and tilting the headrest until the head of the patient is bowed and the neck of the patient is elongated. The operator then locks the hinges 124, 126 to maintain the neck orientation. The headrest 114 can be rotated from 0° to 90° relative to the vertical axis 107. For thoracic and lumber procedures, the angle of neck orientation is adjusted according to the patient and procedural comfort. For cervical procedures, the neck orientation is angled to a maximum curvature.

The thoracic/lumbar support subassembly 146 is unlocked and moves along the support post 106 to align the thoracic support cushion 148 with the anterior thoracic spine of the patient. The thoracic/lumbar support subassembly 146 is then locked to maintain the determined height. The support bar 150 is then unlocked to move horizontally. The thoracic support cushion 148 is pressed against the patient until the patient flexes his/her spine outwards and hunches over the cushion 148. The support bar 150 is locked to maintain the horizontal cushion 148 position. At this orientation, the cervical thoracic, and lumbar spine regions are supported and stabilized by the positioning device and the operator may then perform a thoracic spinal procedure, for example, a thoracic epidural.

FIGS. 1A-1D also show four locking rods and a locking tongue that engage the connection areas 111 of the support post 106. A first locking rod 165 engages the first connection area 111a. A second locking rod 166 engages the second connection area 111b. A third locking rod 167 engages the third connection area 111c. A fourth locking rod 168 engages the fourth connection area 111d and a fifth locking tongue 202 engages the fifth connection area 111e.

Figure 2A:
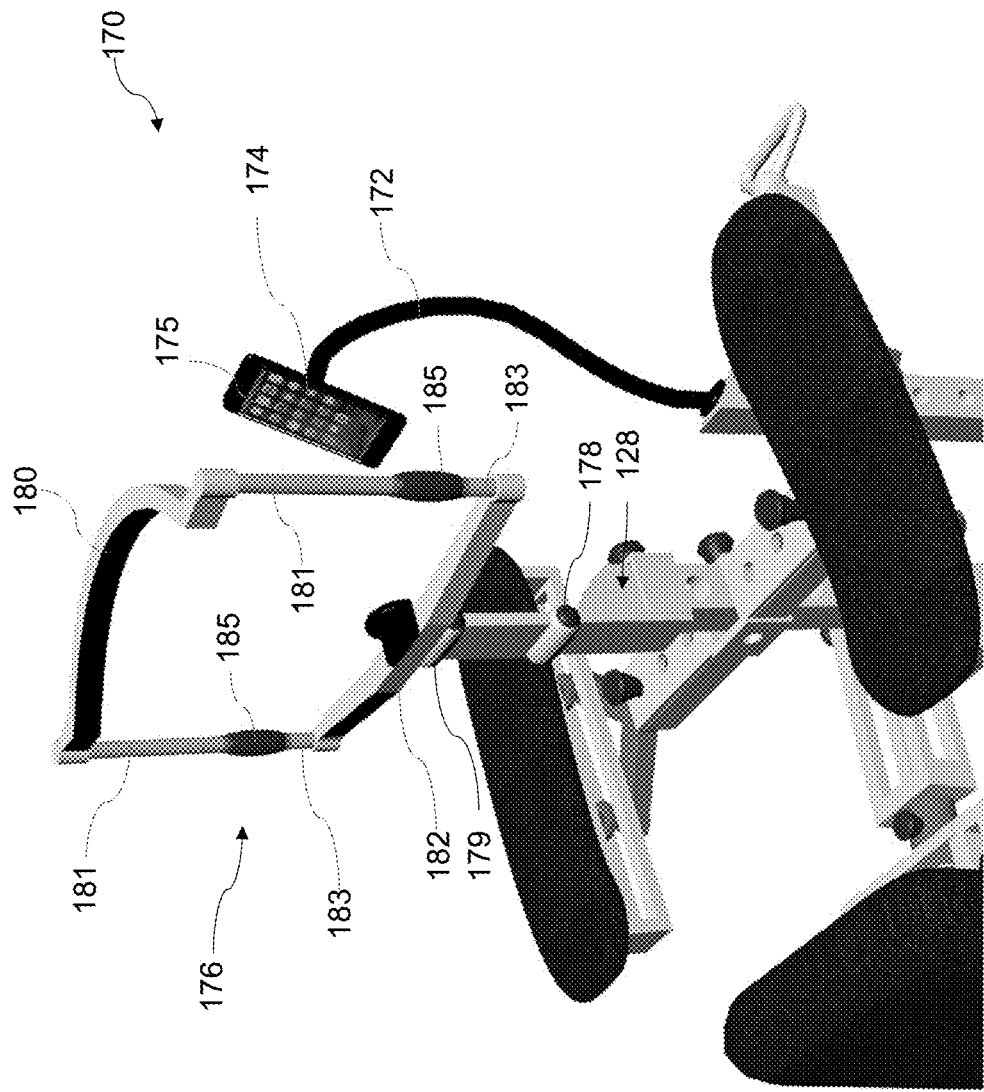
FIGS. 2A and 2B are perspective views of an example of a detachable headrest subassembly of the positioning device having a flexible arm.
Figure 2B:
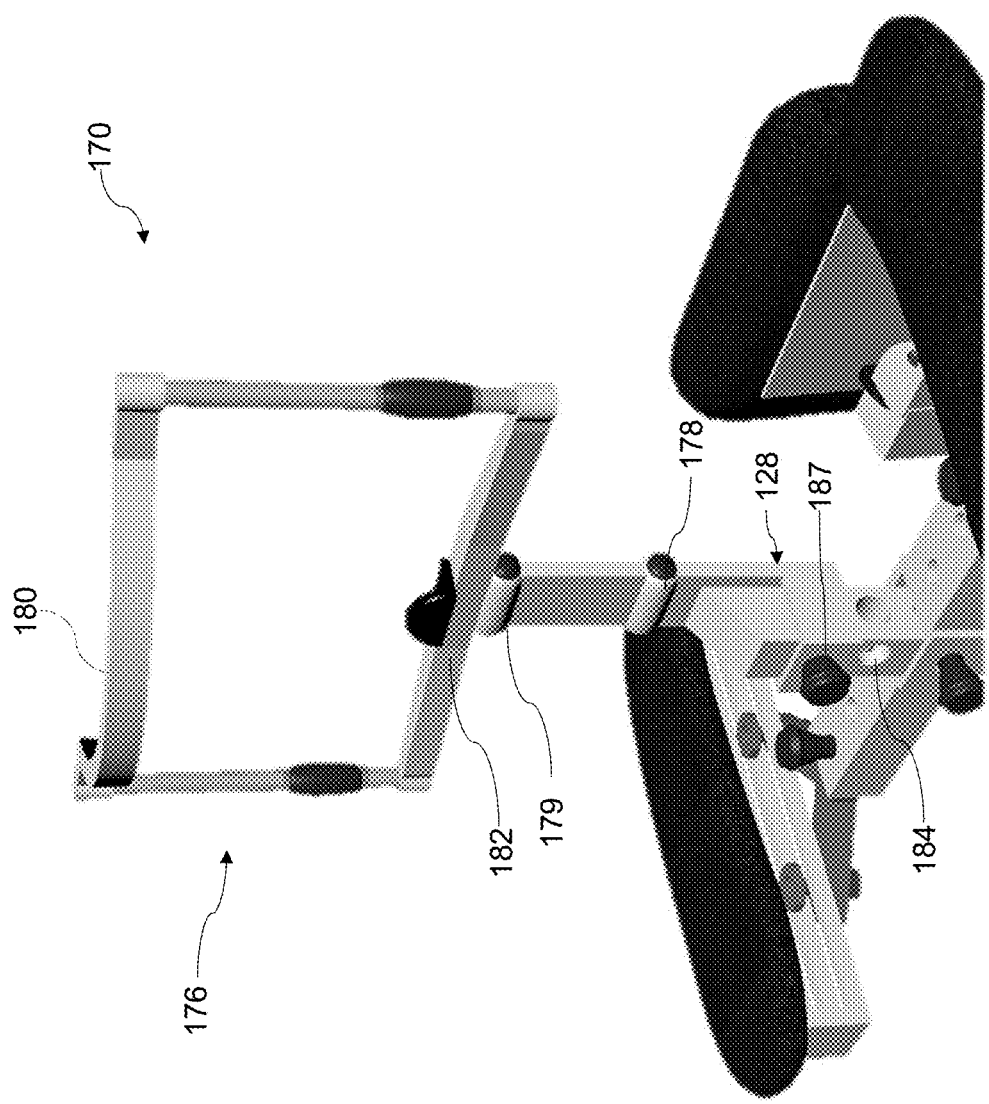

FIGS. 2A and 2B are perspective views of a detachable headrest subassembly 170 and flexible arm 172 of the positioning device 100. A digital device holder 174 attaches to the positioning device 100 by the flexible arm 172. The flexible arm attaches to the second tine 106c. The flexible arm 172 supports a digital device 175 in view of the patient during use of the positioning device 100. The digital device 175 may be a computing device with a display, such as a tablet, a mobile phone, a phablet computer, or any other computing device. The digital device 175 displays instructions to demonstrate the correct body orientation. The digital device 175 also includes translation tools to facilitate conversation between the operator and the patient. Some digital devices are used to distract the patient during the procedure by playing videos, songs, or reading material.

The headrest subassembly 170 is substantially similar to the headrest 114. However, the headrest subassembly 170 includes a square headrest 176 connected to the rod 128 using a single hinge 179, rather than the frame 118, two horizontally aligned hinges 124, 126, and the C-shaped headrest 114. The headrest 176 includes a forehead contact 180 and a chin contact 182. When the patient places his/her head in the headrest 176, only the chin and forehead of the patient abuts the headrest 176. The sides of the face are free. The headrest 176 can rotate about the hinge 178 on the rod 128 and/or the hinge 179 connecting the rod 128 and the headrest 176. This configuration stabilizes the cervical spine and provides a wider field of view. However, in cervical epidural injections, the C-shaped headrest 114 may provide increased accuracy when compared to headrest 170.

Two upper headrest rods 181 extend from the forehead contact 180 and two lower headrest rods 183 extend from the chin contact 182. The upper headrest rods 181 and the lower headrest rods 183 are connected by threaded tubes 185 that are permanently attached to the lower headrest rods 183 and threadedly attached to the upper headrest rods 181. The threaded tubes 185 are axially coupled to the lower headrest rods 183 but are free to rotate relative to both the upper headrest rods 181 and the lower headrest rods 181. When the threaded tubes 185 rotate, the upper headrest rod translates vertically due to the threaded engagement, to bring the chin contact 182 and the forehead contact 180 close together or farther apart. An operator may do this when the head of the patient is too large or too small for the headrest 176. In some headrests, the threaded tubes are in threaded engagement with the lower headrest rods rather than the upper headrest rids. In some headrests, the chin contact and the forehead contact move together using notches and tongues, gear wheels, electric motors, magnetic force, or any combination thereof.

The headrest 176 rotates about the hinge 178 from 0° to 90° relative to the vertical axis 107. The head rest also rotates about the hinge 179 to further flex the cervical spine. The hinges 178, 179 are lockable to lock the headrest at an angle. In FIG. 2A, the headrest 176 is locked at a 0° angle relative to the vertical axis 107. In FIG. 2B, the headrest 176 is locked at an acute angle relative to the vertical axis 107. Some headrests rotate 0° to 90° relative to the vertical axis. In some headrest assemblies, the headrests rotate 0° to 180° relative to the vertical axis. In some headrest assemblies, the hinges are ball joints that allows rotation about the vertical axis and rotation about an axis perpendicular to the vertical axis.

The rod 128 of the headrest subassembly 170 includes a headrest locking hole 187 that extends through the rod 128. The headrest locking hole 187 is perpendicular to the vertical axis 107 and aligns with holes 184 of the first connection area 111a when translated along the vertical axis 107 within hollow first tine 106b of the support post 106. The first locking rod 165 is engages with the headrest locking hole 187 of the rod 128 and the holes 184 of the first connection area 111a to secure the headrest subassembly 170 to the support post 106 at a specific height. Both FIGS. 2A and 2B show the headrest subassembly 170 in the locked position. In the unlocked position, the first locking rod 165 is not engaged and the headrest subassembly 170 is free to translate along the vertical axis within the first tine 106b. In the unlocked position, the headrest subassembly 170 can be removed from the support post 106 entirely, for example if an operator determines that the C-shaped headrest 114 would provide better support.

Figure 3:
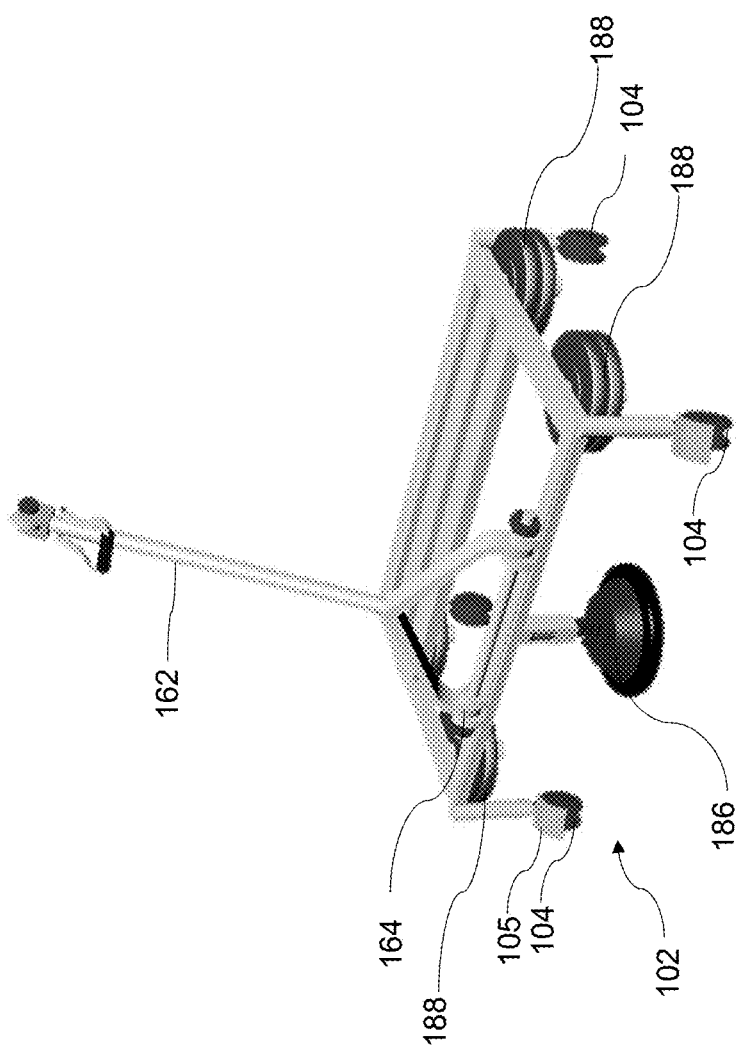
FIG. 3 is a perspective view of an example base of the positioning device with wheels and a handle.

FIG. 3 is a perspective view of the movable base 102 of the positioning device 100 with rollers 104 (or wheels) and the handle 162. The base 102 is arranged about 6 inches (e.g., any value between 4 inches and 8 inches) off the floor. The handle 162 extends opposite the headrest subassembly 112 and rotates about a hinge 164. In some positioning devices, the handle has a limited range of motion, for example, −30° to 90° relative to the vertical axis 107. The handle 162 is used to easily move or position the device without applying force to the attached subcomponents.

A suction cup 186 (or vacuum cup) extends from the base 102 towards a floor to stabilize the positioning device 100 in use. The floor is a horizontal, flat surface. The suction cup can move from an undeployed position to a deployed position. In the deployed position, the suction cup 186 abuts the floor and creates a seal so that the position device 100 remains static. In the undeployed position, the suction cup 186 does not abut the floor and does not prevent the positioning device 100 from moving. In some embodiments, an actuator moves the suction cup between the deployed position and the undeployed position. The actuator may be, for example, a spring, a hydraulic mechanism, an electronic mechanism, lever, or a combination thereof, that can move the suction cup towards the floor and away from the floor. To move the position device, the operator unlocks the wheels 104, and moves the suction cup 186 into the undeployed position. The operator then moves the device 100 to the patient and once arranged at the correct position relative to the patient, the operator then locks the wheels 104 and deploys the suction cup 186. The base 102 also includes multiple weighted plates 188 arranged equally at each corner of the base 102. The plates 188 stabilize and balance the device 100 in use. The plates have a total weight of 5 kilograms (kg), however, some bases may have plates weighing more or less than 5 kg. In some embodiments more plates can be added to the base 10 or removed from the base based on the weight of the patient. On the base 102, the plates 188 are distributed such that one half of the base 102 holds 2.5 kg and the other half of the base holds 2.5 kg.

Figure 4:
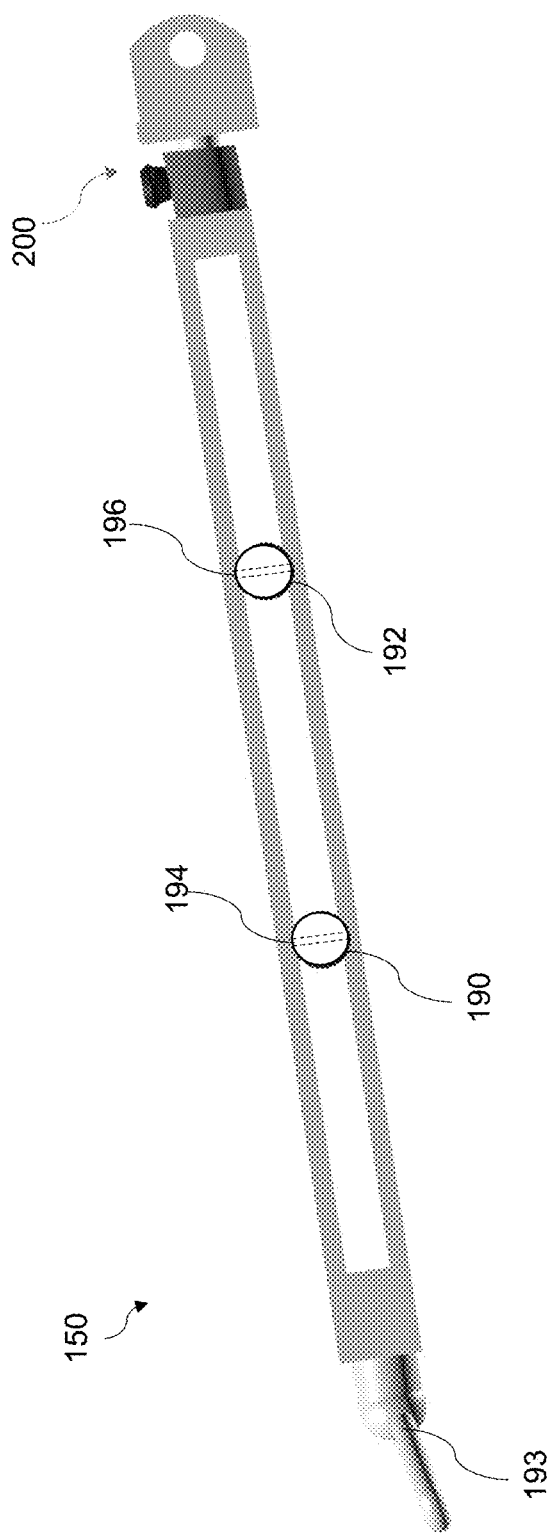
FIG. 4 is a top view of a bar of an example thoracic support subassembly of the positioning device.

FIG. 4 is a top view of the support bar 150 of the thoracic/lumbar support subassembly 146 of a positioning device 100. The support bar 150 is extendable and has a first aperture 190 and a second aperture 192.

Figure 6:
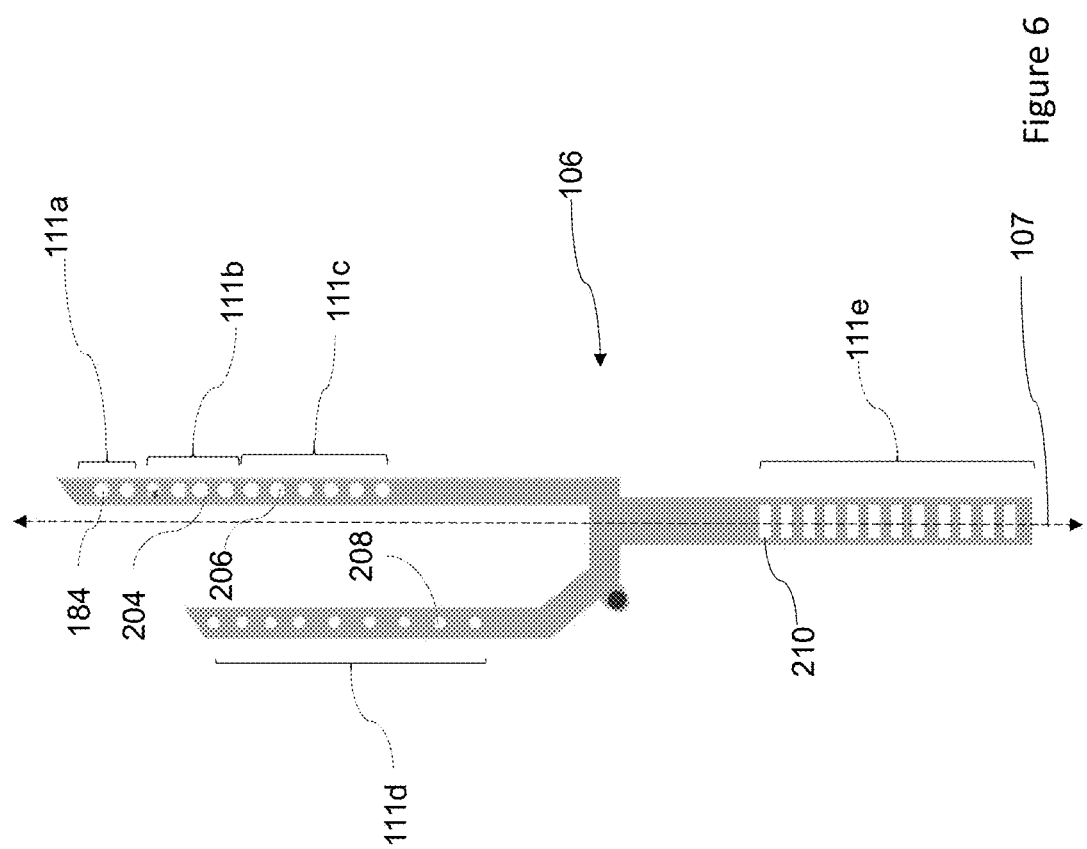
FIG. 6 is a side view of a support post of the positioning device.

The first aperture 190 of the support bar 150 receives the first tine 106b at the third connection area 111c and the second aperture 192 of the support bar 150 receives the second tine 106c at the fourth connection area 111d. A first thoracic locking hole 194 extends perpendicularly though the first aperture 190 and receives the third locking rod 167. To lock the first aperture 190 of the support bar 150 in place, the first thoracic locking hole 194 aligns with a connection hole 206 (shown on FIG. 6) of the third connection area 111c of the support post 106. The first thoracic locking hole 194 and the connection hole 206 receive the third locking rod 167 to lock the thoracic/lumbar support subassembly 146 at a specific height on the support post 106. In the unlocked position, the thoracic/lumbar support subassembly 146 can translate along the third connection area 111c. The third connection area 111c has a plurality of connection holes 206 at different heights along the first tine 106b, as shown in FIG. 6.

The second aperture 192 of the support bar 150 receives the second tine 106c at the fourth connection area 111d. A second thoracic locking hole 196 extends perpendicularly though the second aperture 192 and receives the fourth locking rod 168. To lock the second aperture 192 of the support bar 150 in place, the second thoracic locking hole 196 aligns with a connection hole 208 (shown on FIG. 6) of the fourth connection area 111d of the support post 106. The second thoracic locking hole 196 and the connection hole 208 receive the fourth locking rod 168 to lock the thoracic/lumbar support subassembly 146 at a specific height on the second tine 106c of the support post 106. In the unlocked position, the thoracic/lumbar support subassembly 146 can translate along the fourth connection area 111d. The fourth connection area 111d has a plurality of connection holes 208 at different heights along the second tine 106c, as shown in FIG. 6. Some support assemblies use push/pull locks.

The thoracic support cushion 148 is connected to an end of the support bar 150 via the lockable hinge 200. The lockable hinge 200 has a range of motion between 0° and 180° relative to the vertical axis 107. The patient applies a force to the hinge 200 that moves the hinge 200 to angle the thoracic support cushion 148. In some embodiments, the hinge is resilient or bolted. In the case of a live hinge, the hinge returns to an initial position when the force of the patient is removed.

Figure 5:
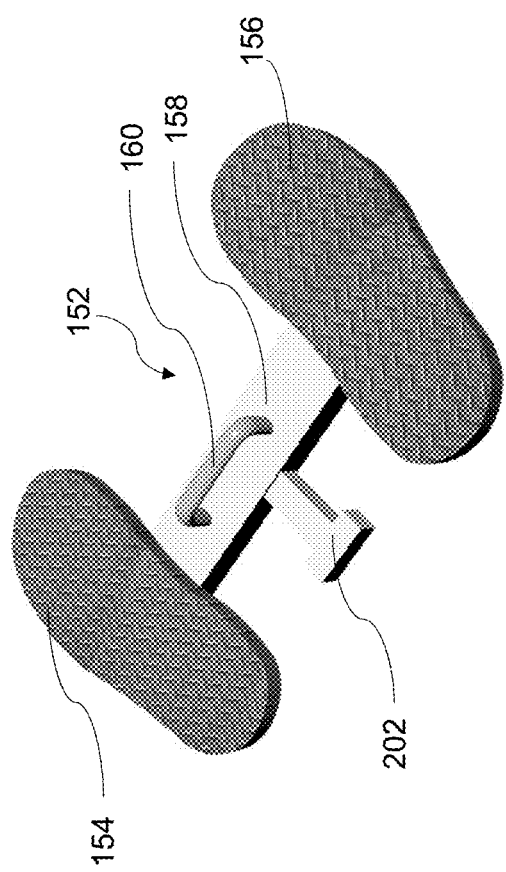
FIG. 5 is a perspective view of an example footrest subassembly of the positioning device.

FIG. 5 is a perspective view of the footrest subassembly 152 of the positioning device 100. A handle 160 is attached to the footrest bar 158. A perpendicular footrest locking tongue 202 is received by the fifth connection area 111e. To lock the footrest subassembly 152 the footrest locking tongue 202 is inserted into one of the connection notches 210 on the fifth connection area 111e. The footrest locking tongue 202 and the connection notches 210 engage to mount the foot rest assembly 152 onto the support post 106. In the unlocked position, the footrest subassembly 152 can translate vertically along the fifth connection area 111e. The user can translate the footrest assembly 152 using the handle 160. The fifth connection area 111e has a plurality of connection notches 210 at different heights long the base section 106a of the support post 106, as shown in FIG. 6.

FIG. 6 is a side view of the support post 106 of the positioning device 100. The first connection area 111a has connection holes 184. The second connection area 111b has connection holes 204. The third connection area 111c has connection holes 206. The fourth connection area 111d has connection holes 208. The fifth connection area 111e has connection holes 210. The connection holes 184, 204, 206, 208, 210 extend vertically along the support post 106 to provide a range of heights for the subassemblies.

Figure 7A:
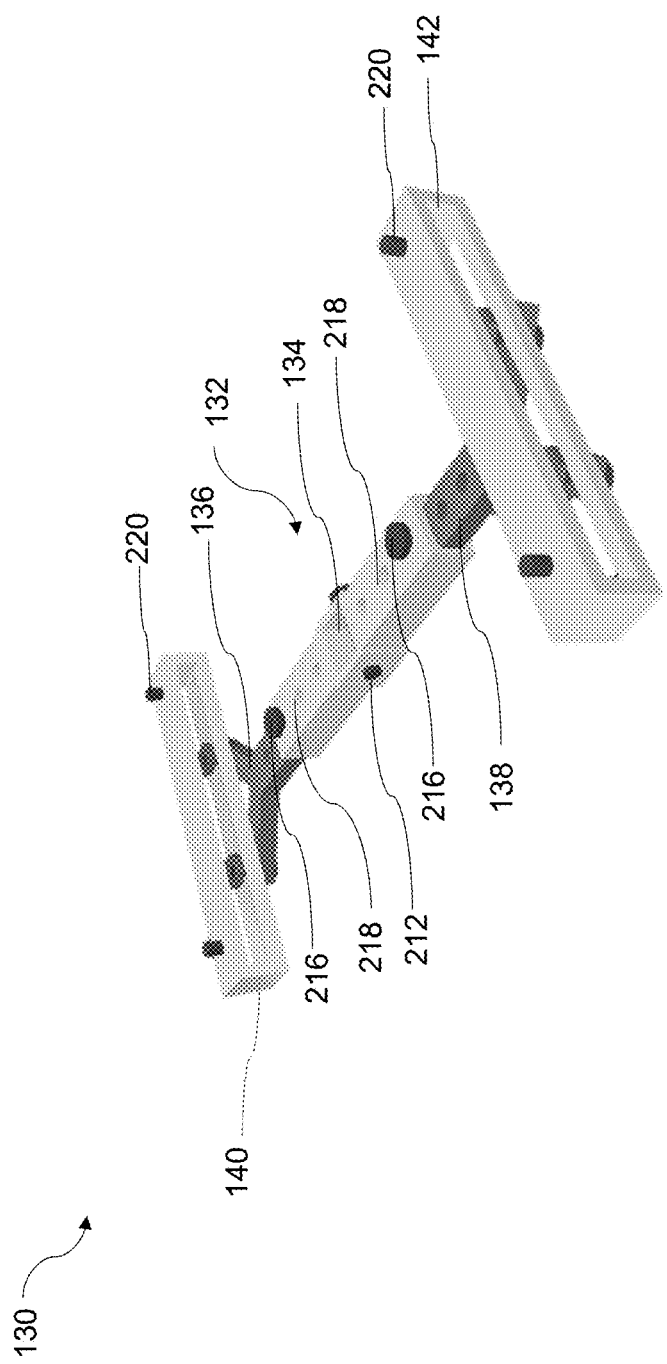
FIGS. 7A and 7B are perspective views of an example arm support subassembly of the positioning device, without and with cushions, respectively.
Figure 7B:
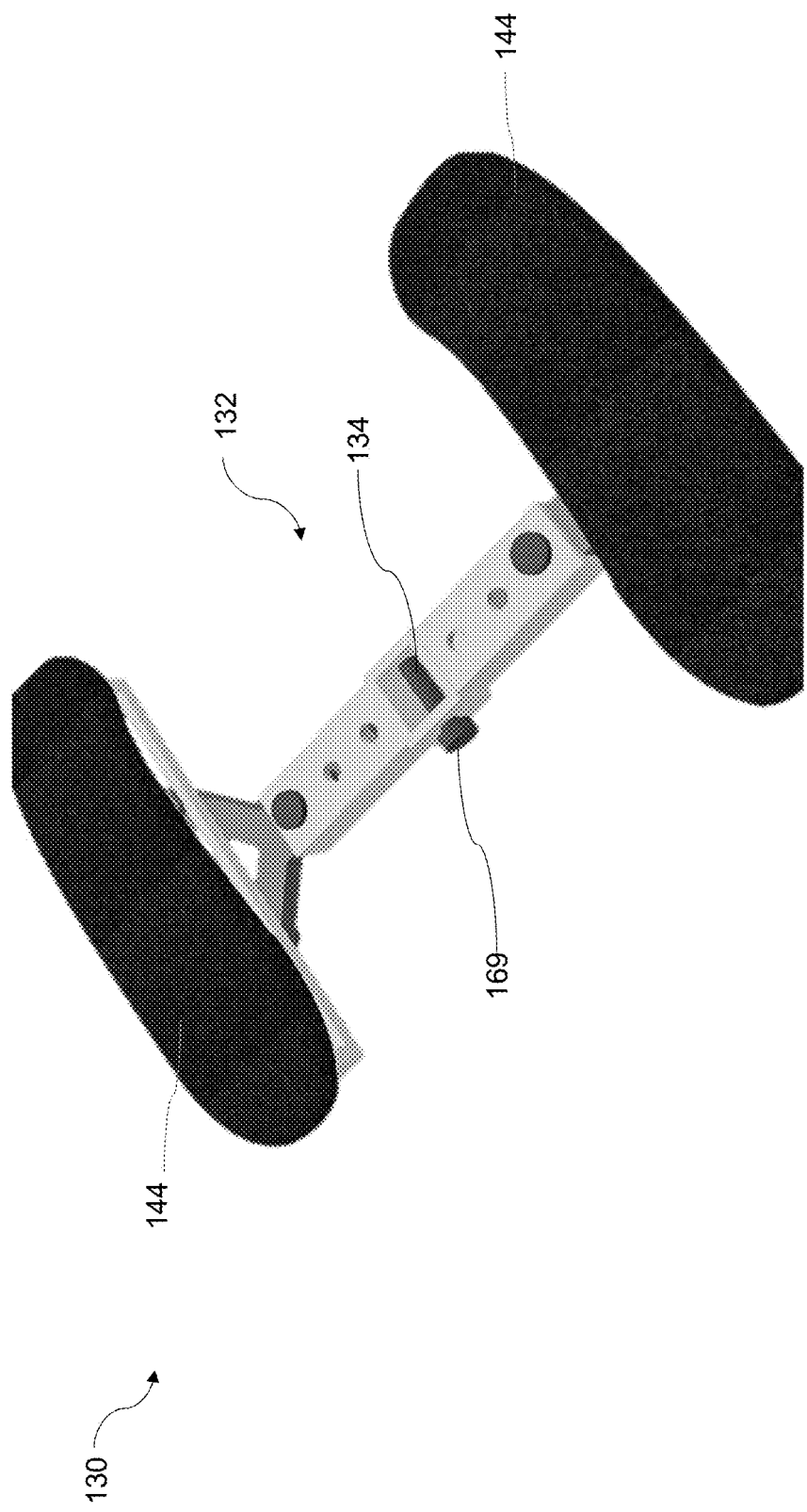

FIG. 7A is a perspective view of the central bar 132 and first plate 140 and second plate 142 of the arm support subassembly 130. FIG. 7B is a perspective view of the arm support subassembly 130 of the positioning device 100 with cushions 144. The central opening 134 includes a perpendicular arm support locking hole 212 sized to receive the second locking rod 166. To lock the arm support subassembly 130 the arm support locking holes 212 align with connection holes 204 on the second connection area 111b. The arm support locking holes 212 and the connection holes 204 receive the second locking rod 166. In the unlocked position, the arm support subassembly 130 can translate along the second connection area 111b. The second connection area 111b has a plurality of connection holes 204 at different heights long the first tine 106b of the support post 106, as shown in FIG. 6. Some arm rest assemblies use push/pull locks.

The central bar 132 is extendable horizontally by inserting pegs 214 into widening apertures 218 in the central bar 132. The pegs 214 extend through the widening apertures 218 to translationally couple the plates 140, 142 to the central bar 150.

The cushions 144 connect to the plates 140, 142 by receiving protrusions 220 that project from the plates 140, 142. Some cushions are attached using magnets or Velcro. Some cushions are adhered to the plates using adhesive.

Figure 8:
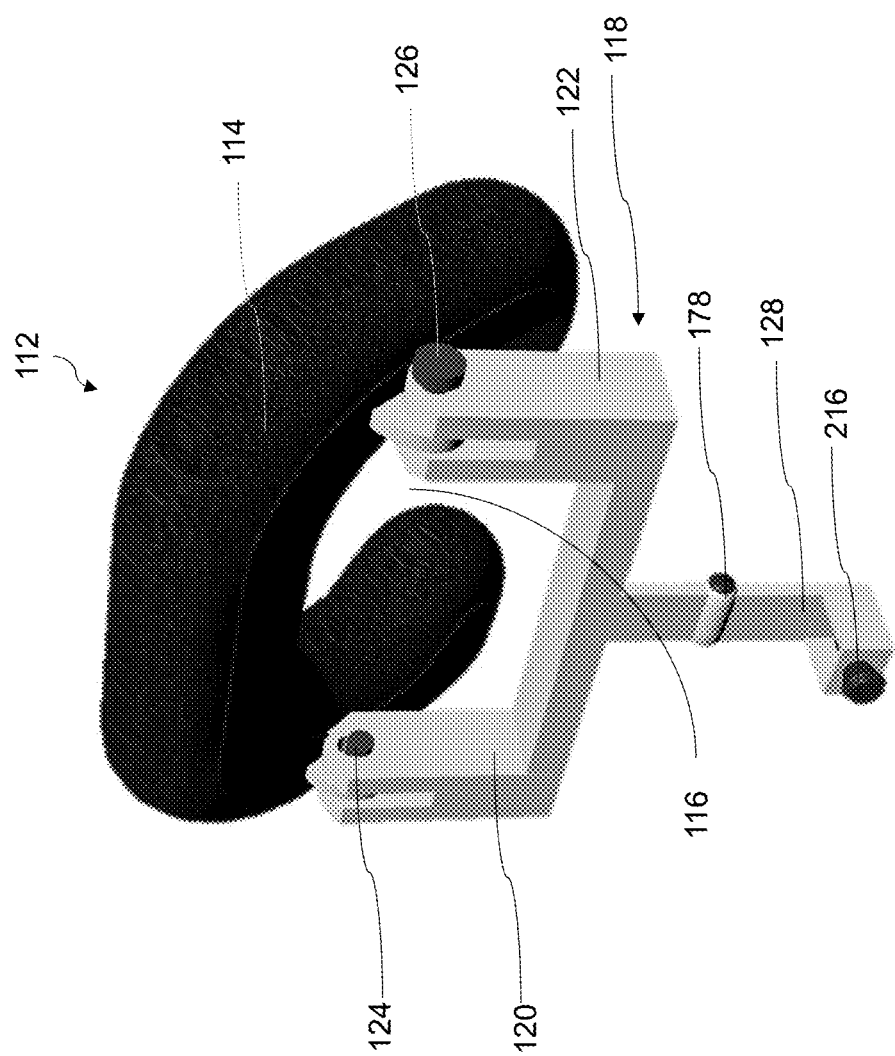
FIG. 8 is a perspective view of an example detachable headrest subassembly of the positioning device.

FIG. 8 is a perspective view of the detachable headrest assembly 112 of the positioning device 100. The headrest subassembly 112 locks and unlocks similarly to the headrest subassembly 170. The rod 128 of the headrest subassembly 112 includes a headrest locking hole 216 that extends through the rod 128. The 216 is perpendicular to the vertical axis 107 and aligns with holes 184 of the first connection area 111a when translated along the vertical axis 107 within hollow first tine 106b of the support post 106. The first locking rod 165 engages with the headrest locking hole 216 of the rod 128 and the holes 184 of the first connection area 111a to secure the headrest subassembly 112 to the support post 106 at a specific height. FIG. 8 shows the headrest subassembly 112 in the locked position. In the unlocked position, the first locking rod 165 is not engaged and the headrest subassembly 112 is free to translate along the vertical axis within the first tine 106b. In the unlocked position, the headrest subassembly 112 can be removed from the support post 106 entirely, for example if an operator determines that the square shaped headrest 176 would provide better support. The head rest assembly further includes the hinge 178 arranged on the rod 128 to more accurately position the cervical spine.

Although a few variations have been described in detail above, other modifications can be possible. For example, to achieve desirable results, one or more sequences of actions described herein may not require the particular sequential order described. Other embodiments may be within the scope of the following claims.

What is claimed is:

1. A positioning device to facilitate positioning of a patient in a sitting position for performance of epidural or spinal procedures, the positioning device comprising:
  a base extending in a horizontal plane;
  a support post attached to the base and extending along a vertical axis;
  a detachable headrest subassembly attached to an end of the support post that is opposite to an end of the support post attached to the base;
  an armrest subassembly attached to the support post between the headrest subassembly and the base;
  a thoracic support subassembly attached to the support post between the armrest subassembly and the base, the thoracic support subassembly comprising a thoracic support cushion attached to the support post by a bar, a first portion of the bar being attached to a first tine of the support post through a first locking rod and a first aperture of the first portion of the bar, a second portion of the bar being attached to a second tine of the support post through a second locking rod and a second aperture of the second portion of the bar, the second tine of the support post being extending in parallel to the first tine, an attachment of the bar to the support post being reconfigurable to vary an orientation and location of the thoracic support cushion with respect to the vertical axis, wherein the thoracic support cushion is configured to directly contact cervical thoracic regions of the patient to provide support to the thoracic spine of the patient;

a footrest subassembly attached to the support post between the thoracic support subassembly and the base; and a digital device holder attached to the support post by a flexible arm, the flexible arm configured to support a digital device in view of the patient during use of the positioning device.

2. The positioning device of claim 1, wherein the headrest subassembly comprises a C-shaped cushion for supporting a head of the patient during use.

3. The positioning device of claim 1, wherein the headrest subassembly comprises a chin support and a forehead support arranged to support a head of the patient relative to the digital device holder to support viewing of the digital device during use of the positioning device.

4. The positioning device of claim 1, wherein the support post comprises a forked portion comprising a pair of tines extending parallel to each other, the pair of tines comprising the first tine and the second tine.

5. The positioning device of claim 4, wherein the thoracic support subassembly attaches to the support post at the tines.

6. The positioning device of claim 5, wherein locations of attachment of the bar to each tine are adjustable.

7. The positioning device of claim 1, wherein the armrest subassembly comprises a pair of armrest cushions separated by a bar attached to the support post.

8. The positioning device of claim 7, wherein a width of the bar separating the armrest cushions is adjustable.

9. The positioning device of claim 7, wherein a position of the bar separating the armrest cushions along the vertical axis is adjustable.

10. The positioning device of claim 1, wherein the base comprises rollers for transporting the positioning device.

11. The positioning device of claim 1, further comprising a handle subassembly attached to the base separate from the support post.

12. The positioning device of claim 1, further comprising a suction cup extending from the base, configured to engage with a receiver.

13. The positioning device of claim 12, wherein the receiver is a floor.

14. The positioning device of claim 13, wherein the floor is a flat, horizontal surface.

15. The positioning device of claim 1, further comprising weighted plates arranged on the base of the position device.

16. The positioning device of claim 1, wherein a portion of the support post is parallel to the vertical axis.

17. The positioning device of claim 1, wherein the first aperture of the first portion of the bar is attached to a first connection hole of the first tine of the support post through the first locking rod, and the second aperture of the second portion of the bar is attached to a second connection hole of the second tine of the support post through the second locking rod, and wherein the first aperture and the second aperture are separated by space along the direction of the bar.

18. The positioning device of claim 17, wherein a first locking hole extending perpendicularly through the first aperture of the first portion of the bar is attached to the first connection hole of the first tine of the support post through the first locking rod, and a second locking hole extending perpendicularly through the second aperture of the second portion of the bar is attached to the second connection hole of the second tine of the support post through the second locking rod.

19. The positioning device of claim 18, wherein the first locking hole is directly attached to and aligned with the first connection hole, and the second locking hole is directly attached to and aligned with the second connection hole.

20. The positioning device of claim 18, wherein the first locking hole and the first connection hole receive the first locking rod, and the second locking hole and the second connection hole receive the second locking rod, and wherein when the position device is used by the patient, the patient sits on a sitting device.

* * * * *